Figure 1B:
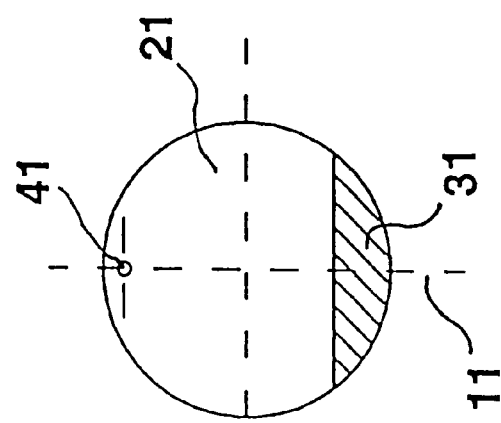

United States Patent
Balazs

[19]

[11] Patent Number: 6,012,494
[45] Date of Patent: Jan. 11, 2000

[54] FLEXIBLE STRUCTURE

[75] Inventor: Matthias Balazs, Grafrath, Germany

[73] Assignee: Deutsche Forschungsanstalt für Luft- und Raumfahrt e.V., Köln, Germany

[21] Appl. No.: 08/617,191

[22] Filed: Mar. 18, 1996

[30] Foreign Application Priority Data

Mar. 16, 1995 [DE] Germany ............... 195 09 116

[51] Int. Cl.$^7$ ................................. F16L 11/14
[52] U.S. Cl. ............... 138/119; 138/110; 138/177; 604/95
[58] Field of Search ............... 138/174, 110, 138/121, 119, 177, 178, 173, 139; 600/128, 141, 143, 149, 150; 604/282, 95

[56] References Cited

U.S. PATENT DOCUMENTS

| | | | |
|---|---|---|---|
| 1,694,430 | 12/1928 | Root | 138/177 |
| 2,962,051 | 11/1960 | Burkes, Jr. | 138/177 |
| 3,109,461 | 11/1963 | Wolff et al. | 138/110 |
| 4,592,231 | 6/1986 | Kant | 138/121 |
| 4,694,547 | 9/1987 | Broussard | 138/177 |
| 4,739,800 | 4/1988 | Baratella | 138/178 |
| 4,791,963 | 12/1988 | Gronert et al. | 138/178 |
| 4,911,206 | 3/1990 | Gropp et al. | 138/178 |
| 5,174,340 | 12/1992 | Peterson et al. | 138/119 |
| 5,325,845 | 7/1994 | Adair | 604/95 |
| 5,381,782 | 1/1995 | DeLaRama et al. | 604/95 |
| 5,449,021 | 9/1995 | Chikama | 138/177 |

FOREIGN PATENT DOCUMENTS 295831  12/1916  Germany.

OTHER PUBLICATIONS

German Patent Abstract (DE3390015), May 11, 1983. Author: Nolles et al.

*Primary Examiner*—Denise L. Ferensic
*Assistant Examiner*—James F. Hook
*Attorney, Agent, or Firm*—Browdy and Neimark

[57] ABSTRACT

In a flexible structure, a number n of notches (12a, 12b) is formed in a preferably circular-cylindrical block of material (1). The parallel and equidistant notches (12a, 12b) begin at two diametrically opposed jacket lines ($10_1$, $10_2$) and are at right angles or an acute angle to the longitudinal axis (10) of the block and are made so deep that for joining together (n+1) segments (22), a continuous, approximately rectangular residual cross-sectional region (32) remains, in the form of a residual web. Symmetrically to the longitudinal axis (10), continuous, closed conduits (52, $52_1$, $52_2$) are formed in the rectangular residual cross-sectional region (32). Moreover, aligned bores ($42_1$, $42_2$) are located at diametrically opposed points, and in them pressure- and/or tension exerting components can be accommodated for bending the flexible structure.

18 Claims, 13 Drawing Sheets

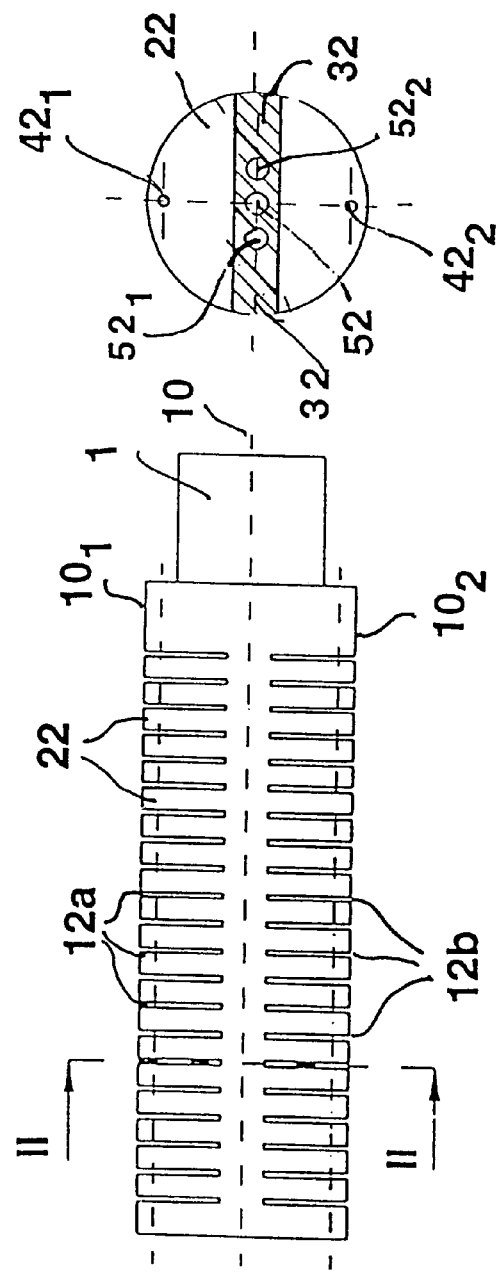

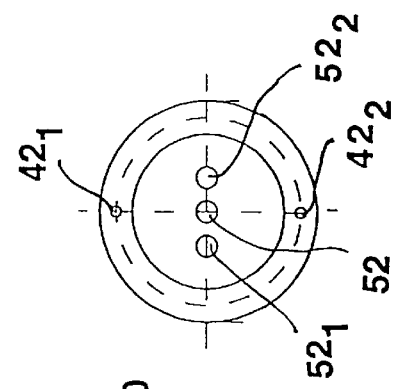
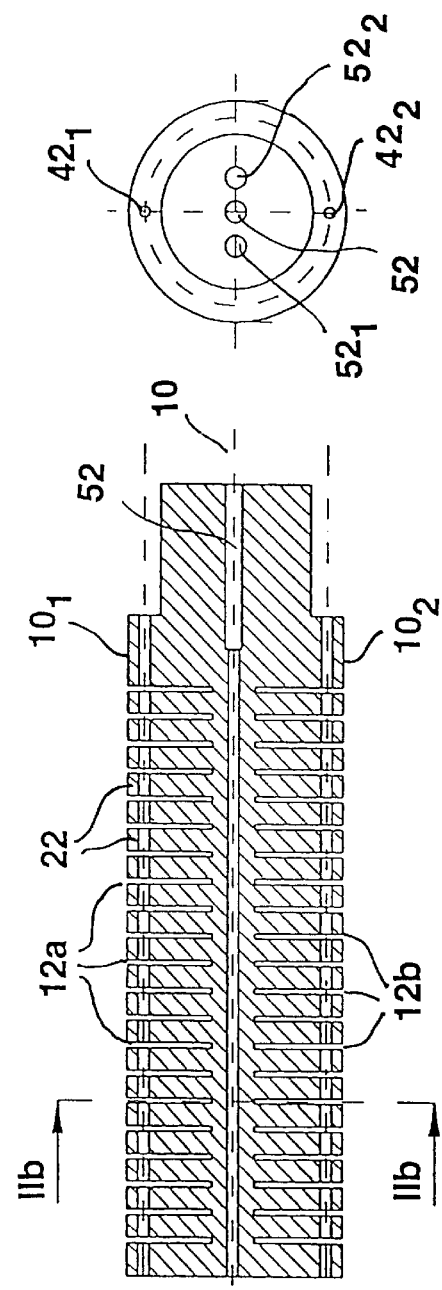
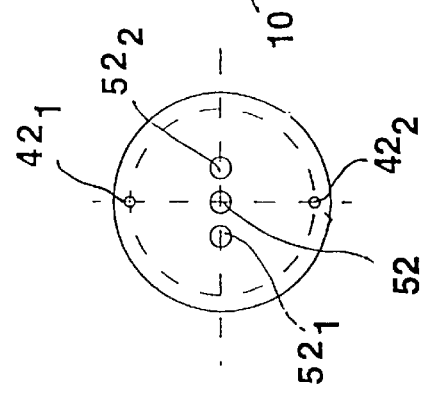

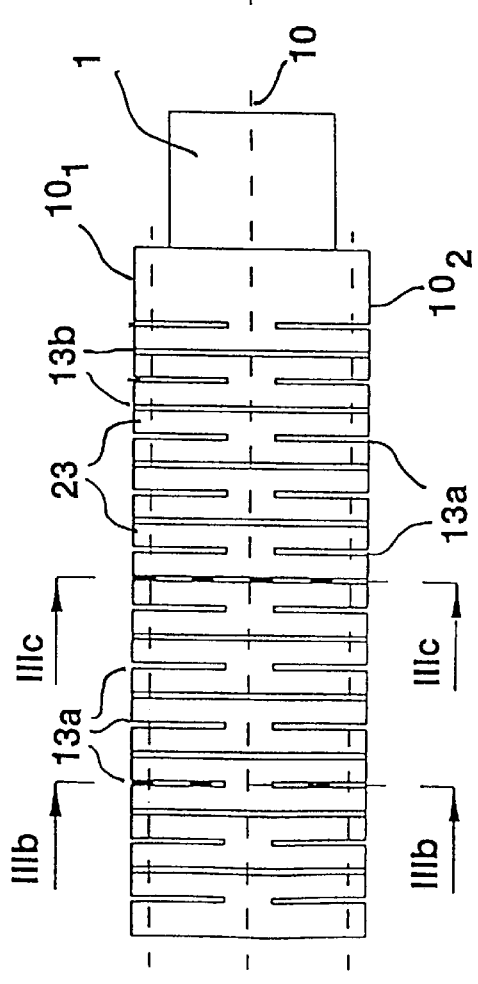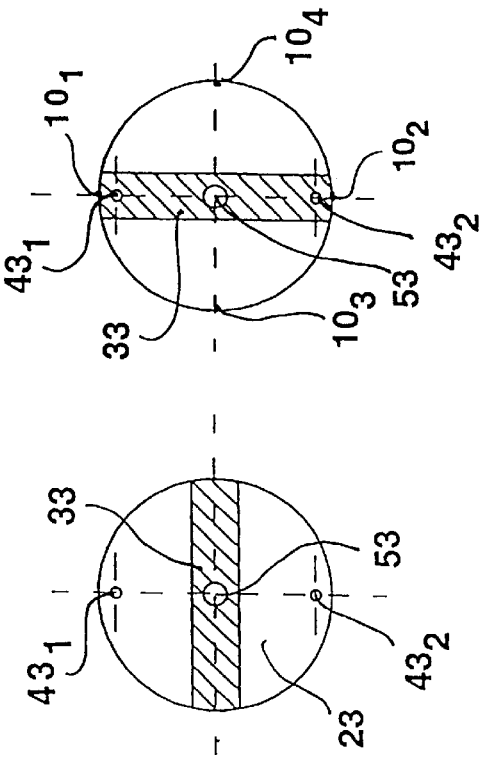

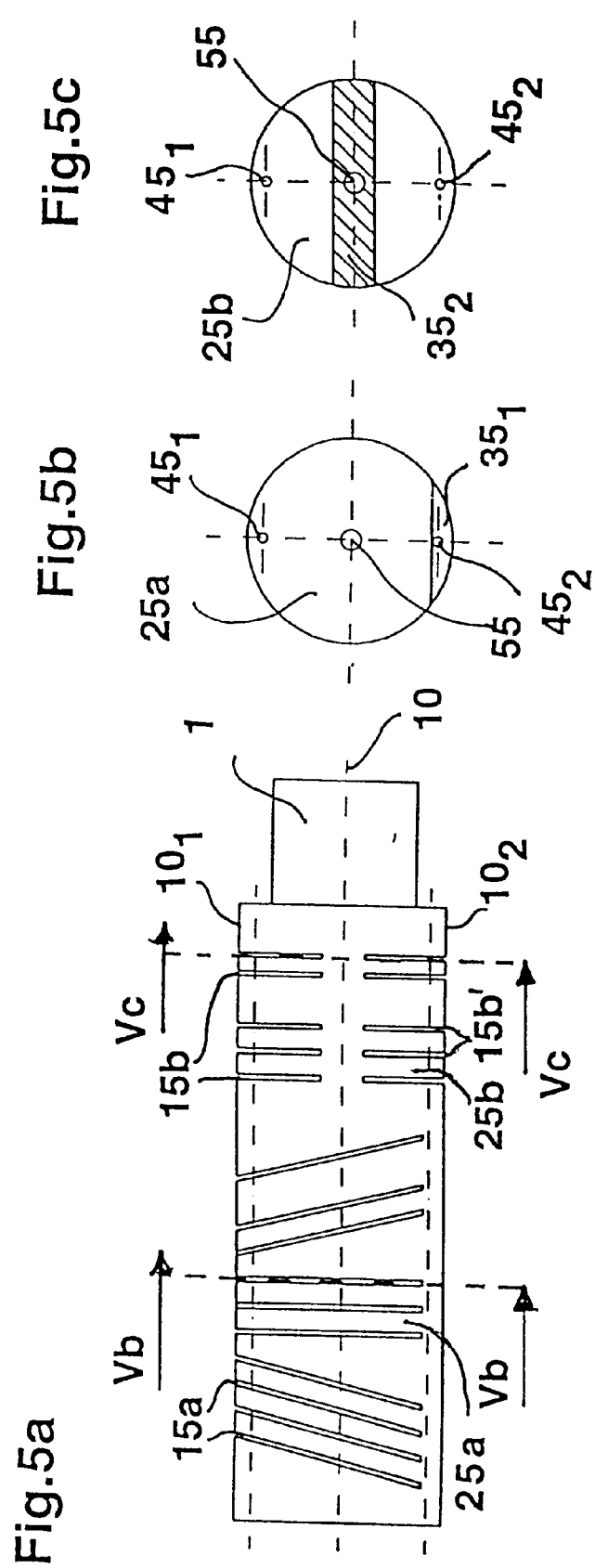

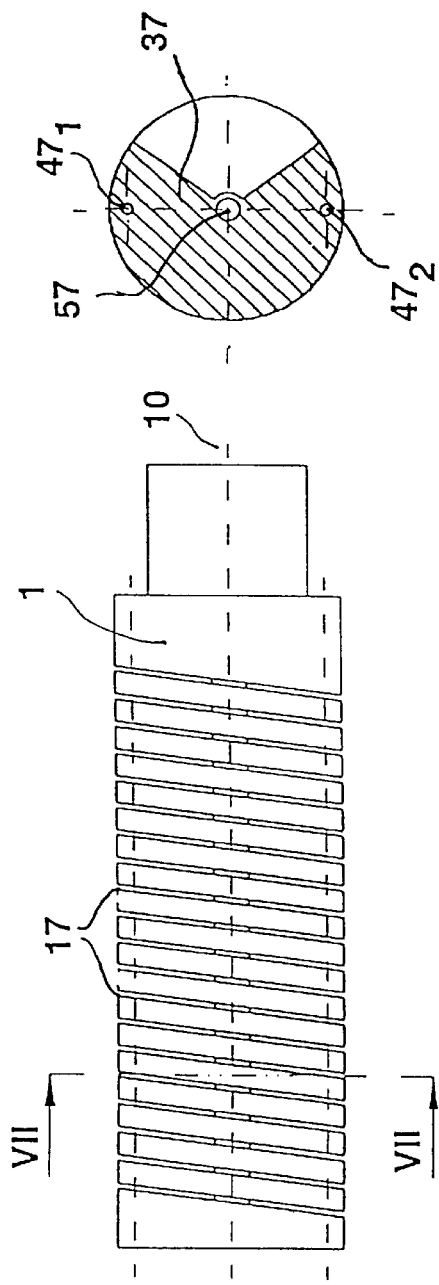

FLEXIBLE STRUCTURE

The invention relates to a flexible structure.

German Patent Disclosure DE 33 90 015 T1, for instance, discloses a radially deflectable, flexible pressure transmission unit, which is mounted on the distal end of a shaft arrangement by means of which actuating elements mounted on its proximal end of a surgical stapler are connected to a stapler placing arrangement of a stapler disposed on the distal end of the pressure transmission device.

With the known pressure transmission device, longitudinal compressive forces can be transmitted. However, a disadvantage of this radially deflectable pressure transmission device is that the structure is composed of a number of individual parts; on the one hand, this is expensive to manufacture, and moreover involves imprecise motion transmission during operation, and furthermore is not accessible to sterilization, because of the many gaps and angles.

German Patent Disclosure DE-OS 29 51 831 describes a component that is relatively firm or stable and is capable of bridging great distances. Plastic deformation is utilized here, in order to form a girderlike member that behaves similarly to an H-girder and is then intended to keep its shape.

According to the invention, a flexible structure is to be created in which both various types of motion kinematics and various additional functions are combined in a single component. According to the invention, this is attained in a flexible structure as defined by the characteristics by claim 1. Advantageous further features are the subject of the claims dependent directly or indirectly on claim 1.

In a flexible structure according to the invention, a block of material is subdivided by n notches into a number of (n+1) segments (where n=1, 2, 3, ... ), which are joined to one another by preserved remaining cross-sectional regions to make a one-piece, bendable structure. Such a structure can preferably be bent or curved in a single plane.

The flexible structure according to the invention is preferably made from a block whose material is preferably a plastic, such as polytetrafluoroethylene (PTFE), polyamide (PA), polyethylene (PE), polyvinylchloride (PVC), and the like. For the flexible structure according to the invention, metal special alloys such as shape memory alloys or titanium alloys can also be used under certain circumstances, as can any other viscoplastic materials.

A plurality of preferably parallel notches are made in the block of material preferably comprising one of the plastics listed above, so that a corresponding freedom of motion is established in or around the remaining residual cross-sectional region. The freedom of motion is dependent on the width of the notches, the depth of the notches, and thus on the remaining residual cross-sectional region, which acts as a kind of flexible strap, as well as on the number, disposition and form of the individual segments.

The preferred plastic material is polytetrafluoroethylene (PTFE), since it has good machinability, good viscoplastic material behavior, very high resistance to alternating bending strains, a very low tendency to deformation or creeping, and particularly with a view to medical applications, it can be cleaned very well. To achieve a bending capability of about 55° to 60°, a number of n=21 notches with a width of 0.5 mm can preferably be made; for an initial crude diameter of 20 mm for the block of material, the continuous residual cross-sectional region has a width of about 2 mm and a thickness also of 2 mm.

On bending by the angle α of up to about 55° to 60°, the peripheral fiber curve lengths, which in the straight, elongated state of the component have a length of l, are shortened or lengthened by Δl, in accordance with the following formula:

$$\Delta l = n \cdot B$$

where Δl indicates a shortening or lengthening, n the number of notches, and B the width of a notch. The notches are preferably disposed equidistantly, and in the flexible structure of the invention a length of $l \geq 5 \cdot \Delta l$ should be adhered to, in order to make good use of the material elasticity in this way.

A notch depth of approximately 0.5·D should also be preferably used, which is equivalent to a web width for the remaining cross-sectional region of approximately 0.1 D; D is the outside diameter of the finished flexible structure. The figures given above relate to PTFE material and are highly dependent on the modulus of elasticity and tensile strength of the material used.

The bending angle α of a flexible structure according to the invention can be calculated by the following formula:

$$\alpha = \frac{\Delta l \cdot 360°}{2 \cdot \pi \cdot D}$$

Here the bending angle is not dependent on the length of the flexible structure but instead on the outer diameter thereof and on the shortening or lengthening Δl. (The formulas shown here do involve a small error, because they do not take into account the effect of the web width.) The resultant bending radius of a flexible structure increases with the width or thickness of the residual cross-sectional regions.

In order to attain various kinematic properties in the flexible structure of the invention, the position, number and form of the notches can be varied, as will be explained in further detail below with reference to a number of embodiments. Moreover, the notches can be arranged arbitrarily relative to one another, preferably parallel and equidistant, or parallel with variable spacing; they may be angled toward one another by the same angle, and may be cut variously deep, for the same or different width of the residual cross-sectional region. Moreover, all the combinations resulting from these positions can be employed.

As a result, the flexible structure of the invention can be made from semifinished products of arbitrary cross sections, an example being elongated semi-finished products with a rectangular cross section, a circular or elliptical cross section, arbitrary polygonal cross sections, arbitrary hollow cross sections, preferably tubes and industrial profiles, semi-finished products with arbitrary cross-sectional shapes and cross-sectional courses of the length of a flexible structure, which is preferably embodied in cone or wedge form, or may have arbitrary constant or nonconstant cross-sectional courses, such as a rectangular cross section that continuously changes toward an ellipsoid cross section.

Another advantage of the flexible structure of the invention is that it can be made in virtually any arbitrary size, especially by means of machining processes, for instance in a miniaturized size or a microsystem-industrial size, where it is preferably made by direct laser machining. Production of the flexible structure of the invention in macroscopic sizes is also possible, preferably in conventional sizes for installation of conduits or pipes and as cable guiding devices.

A part size of the kind usual for tunnel construction components, or sewer pipes, is also possible. Moreover, the flexible structure of the invention can be made in sizes of the kind used in robotics, which in turn then ranges from microsystem technology perhaps to robots the size of a house, used for dismantling nuclear power plants.

It is also especially advantageous in the flexible structure of the invention that the following different forms of motion are achievable, namely bending in one plane, in one direction or in two directions, beginning with the straight or elongated state; bending in two planes in arbitrary directions; rotation about an axis; screwing about an axis; and shortening or lengthening in one axial direction, with the outer form of the flexible structure of the invention allowing arbitrary cross-sectional courses.

In the flexible structure of the invention, by means of suitable structuring of components, various passive additional functions can also be integrated with it, such as conduits for receiving lengths of cable or rope, for bending the flexible structure, suction and flushing conduits, conduits for accommodating lasers, fiber optics and lighting devices and/or surgical tools, for instance in minimally invasive surgery (MIS).

Conduits for receiving drive mechanisms for instruments or devices that must be controlled through the flexible structure, such as gripper arms, forceps, scissors or other actuators, can also be formed. Furthermore, cable conduits can be provided in the flexible structure of the invention, so that coagulating HF current can be carried in insulated fashion or to provide end effectors by means of electric motor drives or electromechanical effects, such as the piezoelectric effect, the magnetostrictive effect, or triggering of shape memory alloys.

With suitable component structuring, arbitrary active additional functions can be integrated, for instance in the form of kinetic properties. To that end, microactuators can preferably be used, which are operative in each segment or are coupled or uncoupled in selected segments. Drive mechanisms can also be integrated with the flexible structure, and as a result the structure is turned into an actuator. The drive mechanisms need not necessarily be accommodated in the flexible structure but instead can also be disposed outside the flexible structure, somewhat as in the case of robot hands with Bowden cable drives.

With the aid of known final control elements, such as linear drives, active versions of the flexible structure can also be realized, such as a drive by means of cables, in order to angle or bend the flexible structure; the cables can be actuated by a linear drive, or alternatively by hand.

The flexible structure of the invention can also be made especially economically, since a plurality of flexible members are joined elastically together in a single component, and the structure can readily be expanded with additional functions, so that integration of even complex functions thus becomes possible. Moreover, the flexible structure of the invention has no conventional, mechanical multi-part joints and therefore remains play-free as long as it is usable. As a result, for a combination with externally or internally mounted drive mechanisms and/or suitable sensors, a structure that remains constant in geometrical terms is created which has no play over its service life.

If the flexible structure is made of PTFE, then it is especially suitable for medical applications, since compared with conventional joint chains an advantageous feature is that between joints, the flexible structure has no gaps that are inaccessible to thorough cleaning. Instead, the flexible structure of the invention can be cleaned and sterilized at high pressure of 4.5 bar and at temperatures of 134° C. and above, without having to be dismantled for the purpose, since both all the notches and the conduits that enable the additional functions can easily be flushed or are completely sealed off anyway.

The flexible structure can also be used outside medical technology, in the most various fields, preferably as a main actuator group in robotics, as carriers of optical elements in flexible endoscopy, and for monitoring hollow spaces, or the structure of the invention can also be used as a flexible guide tube for arbitrary industrial and even nonindustrial use.

Figure 1A:
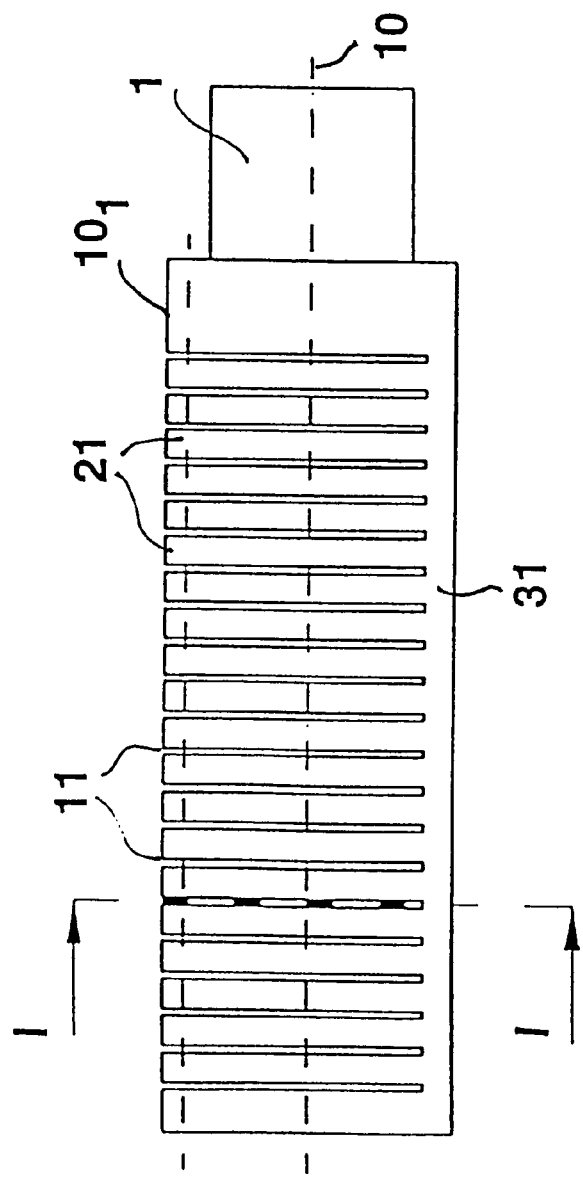
Figure 4C:
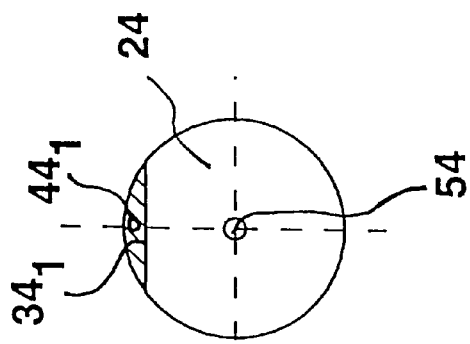
Figure 4B:
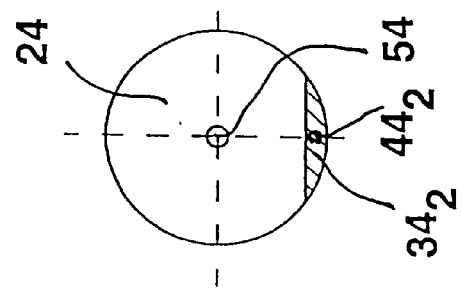
Figure 4A:
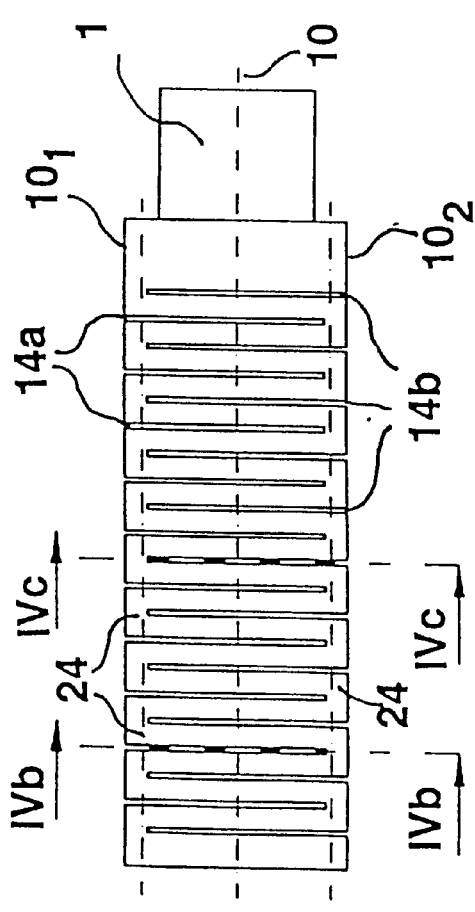
Figures 6A, 6B:
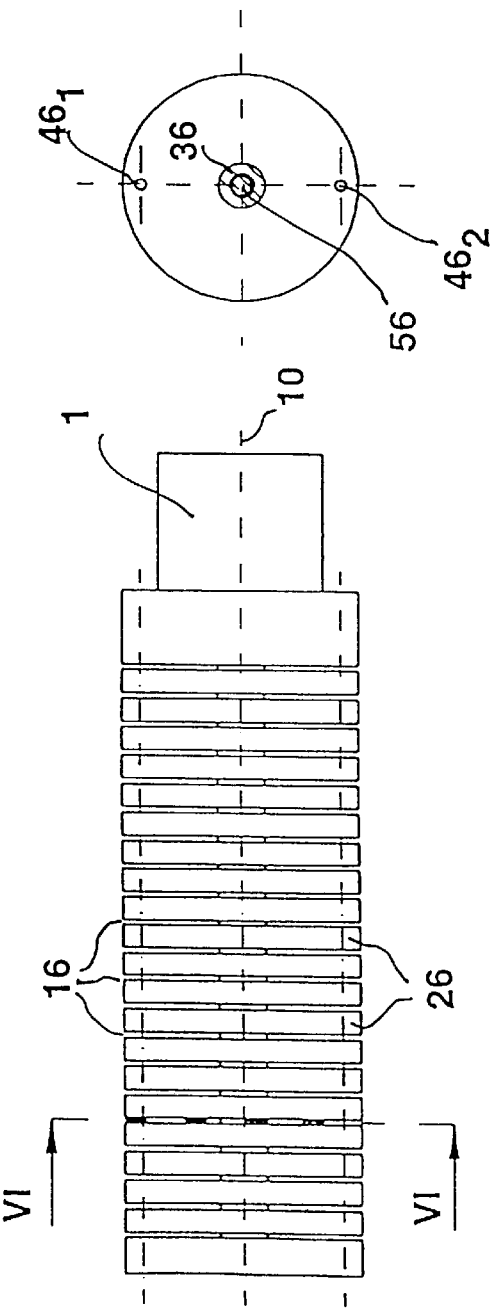
Figure 8:
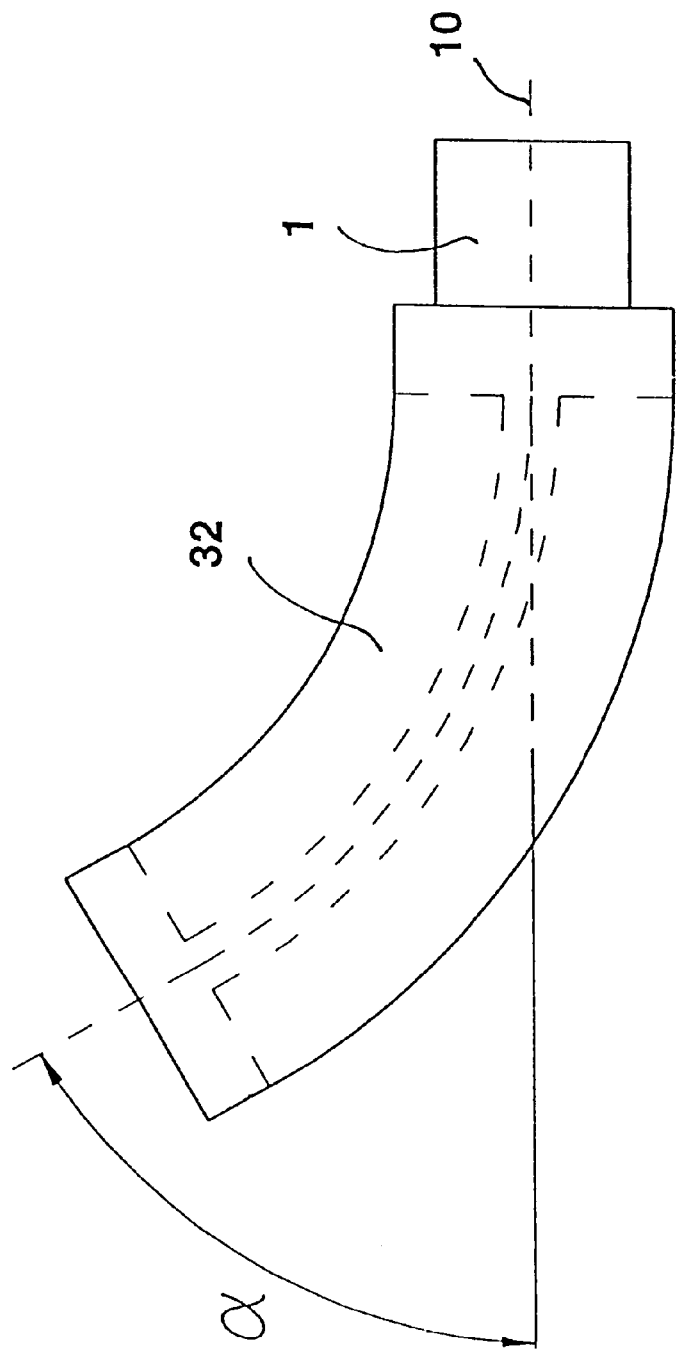
Figure 9:
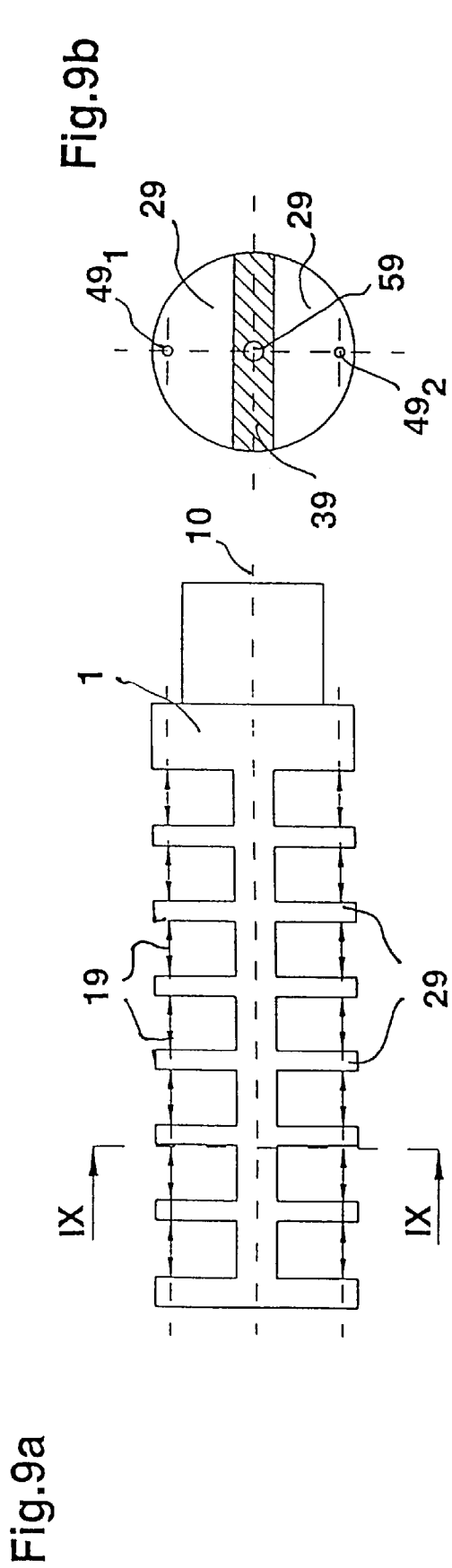
Figure 10:
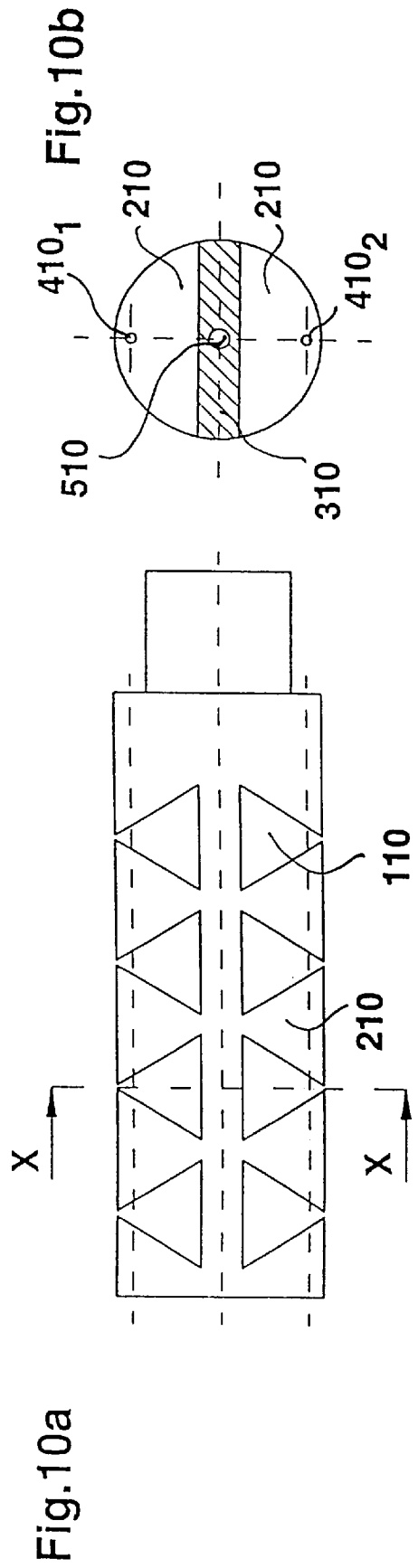
Figure 11:
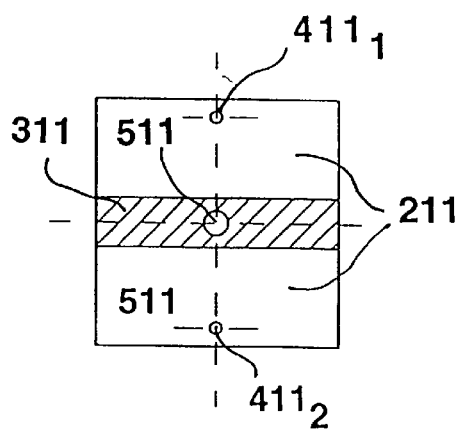

The invention will be described in detail below in terms of preferred embodiments, with reference to the accompanying drawings. Shown are:

FIG. 1a, a schematic sectional view of a first embodiment of a flexible structure according to the invention;

FIG. 1b, a sectional view taken along a line I—I in FIG. 1a;

FIG. 2a, a schematic sectional view of a second embodiment of a flexible structure according to the invention;

FIG. 2b, a sectional view taken along a line II—II in FIG. 2a;

FIG. 2c, a longitudinal section through the second embodiment schematically shown in FIG. 2a;

FIG. 2d, a plan view of the right-hand end face, in FIG. 2c, of the longitudinal sectional view;

FIG. 2e, a plan view on the left-hand end face in FIG. 2c;

FIG. 3a, schematically, a third embodiment of the flexible structure of the invention;

FIGS. 3b and 3c, sectional views along a line IIIb—IIIb and IIIc—IIIc, respectively;

FIG. 4a, a schematic plan view on a fourth embodiment of the flexible structure according to the invention;

FIGS. 4b and 4c, sectional views along a line IVb—IVb and IVc—IVc, respectively, in FIG. 4a;

FIG. 5a, schematically, a fifth embodiment of a flexible structure according to the invention;

FIG. 5b, a sectional view along a line Vb—Vb of FIG. 5a;

FIG. 5c, a sectional view along a line Vc—Vc of FIG. 5a;

FIG. 6a, a sixth embodiment of the flexible structure of the invention;

FIG. 6b, a sectional view along a line VI—VI of FIG. 6a;

FIG. 7a, schematically, a seventh embodiment of a flexible structure according to the invention;

FIG. 7b, a sectional view along a line VIIb—VIIb of FIG. 7a;

FIG. 8, a schematic view of a flexible structure of FIGS. 2a, 3a, 6a or 7a in the bent state;

FIG. 9a, schematically, a eighth embodiment of a flexible structure according to the invention;

FIG. 9b, a sectional view along a line IXb—IXb of FIG. 9a;

FIG. 10a, a ninth embodiment of the flexible structure of the invention;

FIG. 10b, a sectional view along a line X—X of FIG. 10a; and

FIGS. 11–23, sectional views taken at right angles to the longitudinal axis through a flexible structure, of further embodiments of the flexible structure according to the invention.

A first embodiment of a flexible structure of the invention will now be described in conjunction with FIGS. 1a and 1b. In a circular-cylindrical block of material 1, n notches 11 are formed parallel to and equidistant from one another and perpendicular to the longitudinal axis 10 of the block, beginning at a jacket line $10_1$ extending parallel to the main longitudinal axis 10. This creates (n+1) segments 21 between the n notches 11; these segments are joined, to form a one-piece bendable structure, by a segmental residual cross-sectional region 31 shown in plan view in the lower portion of FIG. 1a and in section in FIG. 1b.

As can be seen from the sectional view of FIG. 1b, the segmental residual cross-sectional region 31 is symmetrical to a line 11, shown in dashed lines in FIG. 1b, that extends at right angles to the longitudinal axis of the block. Unlike the course of the notches 11 shown in FIG. 1a, notches can also be made in the block of material 1 at an acute angle from the longitudinal axis 10 of the block, equidistant from one another or at various spacings from one another.

The above statement applies in principle to all the embodiments shown in the drawings and for this reason will not be repeated each time a different embodiment is described below. To enable angling or bending the flexible structure, for instance in the manner shown in FIG. 8, a bore 41 parallel to the longitudinal axis 10 is shown, for the first embodiment shown in FIGS. 1a and 1b, at a point opposite the segmental residual cross-sectional region 31; means that exert tension for bending the flexible structure can be accommodated in this bore.

In the second embodiment of a flexible structure, shown in FIGS. 2a and 2b, unlike the first embodiment shown in FIGS. 1a and 1b, these n notches 12a and 12b are parallel and equidistant and are disposed at right angles to the longitudinal axis 10 of the block of material 1, beginning at two diametrically opposed jacket lines $10_1$ and $10_2$. The notches 12a and 12b are made deep enough that for the (n+1) segments 22 between the opposed ends of the two groups of notches 12a and 12b, a continuous, approximately rectangular residual cross-sectional region 32 in the form of a residual web remains, as can be seen from the sectional view of FIG. 2b.

A continuous, closed conduit 52 is formed symmetrically to the longitudinal axis 10 in the rectangular residual cross-sectional region 32, as can be seen from the longitudinal section of FIG. 2c. Other bores $42_1$ and $42_2$, aligned with one another, are also formed symmetrically to the conduit 52 at diametrically opposed points, and in these bores pressure- and/or tension-exerting means, not shown in detail, for bending the flexible structure can be accommodated. To form suction and/or flushing conduits, as well as conduits for receiving fiber optics and the like, one or more additional conduits $52_1$ and $52_2$ may be formed on one or both sides of the continuous, centrally placed conduit (52).

In FIGS. 3a–3c, n notches 13a and 13b in the circular-cylindrical block of material 1 each begin alternatingly at two diametrically opposed jacket lines $10_1$–$10_4$, which as can be seen from FIGS. 3a and 3c are offset from one another by 90° along a circular circumferential line of the block of material 1. In FIG. 3a, the n notches, again parallel and equidistant, are again disposed at right angles to the longitudinal axis 10. Here the n notches 13a and 13b are made deep enough that on the opposed ends of the two groups of notches 13a and 13b offset by 90°, an approximately square residual cross-sectional region 33 remains, symmetrical to the longitudinal axis 10 of the block, as shown by dashed lines in the sectional views of FIGS. 3b and 3c. As can also be seen from the two sectional views of FIGS. 3b and 3c, one continuous, closed conduit 53 and diametrically opposed bores $43_1$ and $43_2$ aligned with one another are formed symmetrically to the longitudinal axis 10.

FIGS. 4a–4c show a fourth preferred embodiment of a flexible structure. Here, the notches 14a and 14b each begin at the two jacket lines $10_1$ and $10_2$, which are diametrically offset, in other words are offset by 180°, along a circular circumferential line of the circular-cylindrical block of material 1. In FIG. 4a, the notches are again aligned parallel and equidistant and are again perpendicular to the longitudinal axis 10. Two of the segments 24 at a time, that is, on the two ends of each notch 14a and 14b, respectively, are joined together by approximately segmental residual cross-sectional regions $34_1$ and $34_2$, which as can be seen from the sectional views of FIGS. 4b and 4c are formed diametrically opposite one another.

Thus once again, a one-piece, bendable structure is created by the two segmental residual cross-sectional regions $34_1$ and $34_2$. Also in the fourth embodiment, a continuous conduit 54 interrupted by the notches 14a and 14b is formed symmetrically to the longitudinal axis 10.

In FIGS. 5a–5c, some of the notches 15b and 15b' again begin at the two opposed jacket lines $10_1$ and $10_2$ and are disposed parallel to one another, with both equal and unequal spacings, at right angles to the longitudinal axis 10, and are made deep enough that, as can be seen from FIG. 5c, an approximately rectangular residual cross-sectional region $35_2$ remains. As shown in the left-hand portion of FIG. 5a, notches 15a begin at the one jacket line $10_1$, extending at various angles and at right angles to the longitudinal axis 10; as can be seen from the sectional view of FIG. 5b, they are made deep enough that in the region of the notches 15a, only a segmental cross-sectional region $35_1$ now remains.

In the fifth embodiment as well, a continuous conduit 55 interrupted by the notches 15a is formed symmetrically to the longitudinal axis 10, and two diametrically opposed, aligned bores $45_1$ and $45_2$ are formed symmetrically to it. Thus, between the notches 15a and 15b, variously wide sections 25a and 25b are formed at different angles relative to the longitudinal axis 10.

In the sixth embodiment shown in FIGS. 6a and 6b, the block of material 1 is embodied as a turned part, in which the notches 16 extend parallel to one another and perpendicular to the longitudinal axis 10 and are separated from one another by intervening segments 26. The segments 26 are joined together by a central, preferably circular residual cross-sectional region 36, so that once again the result is a one-piece, bendable, flexible structure.

A continuous closed conduit 56 is provided in the circular residual cross-sectional region 36, and diametrically opposed aligned bores $46_1$ and $46_2$ are provided, for instance for accommodating tension- or pressure-exerting means.

Unlike the sixth embodiment shown in FIGS. 6a and 6b, in the seventh embodiment of a flexible structure in FIGS. 7a and 7b, a cohesive, continuous, helical-line-form notch 17 is formed in the block of material 1. Once again an approximately circular residual cross-sectional region 37 remains, located symmetrically to the longitudinal axis 10, and in it centrally a continuous closed conduit 57 is formed. Once again on both sides of the centrally disposed conduit 57, there are diametrically opposed bores 47 and $47_2$ aligned with one another.

In FIGS. 9a and 9b, an eighth embodiment of a flexible structure is shown, in which to accommodate one or more actuators, the width of the notches 19 between the segments 29 disposed at right angles to the longitudinal axis 10 amounts to a multiple of the width of the segments, and the notches are rectangular or square in cross section. In this embodiment as well, a continuous, closed conduit 59 is formed centrally in the remaining, approximately rectangular residual cross-sectional region 39, and diametrically opposed, aligned bores $49_1$ and $49_2$ are provided relative to this conduit.

Unlike the embodiment of FIGS. 9a and 9b, notches 110 in the ninth embodiment, shown in FIGS. 10a and 10b, have the form of a triangle, preferably an equilateral triangle, in cross section. Between these notches 110 of triangular cross section, segments 210 complementary to them are provided. Otherwise, the embodiment shown in FIGS. 10a and 10b is equivalent to the embodiment shown in FIGS. 9a and 9b, which is expressed by the fact that aside from the residual cross-sectional region 310 in FIG. 10b, the other reference numerals now end not with the digit 9 as in FIG. 9b but with the number 10.

Figure 12:
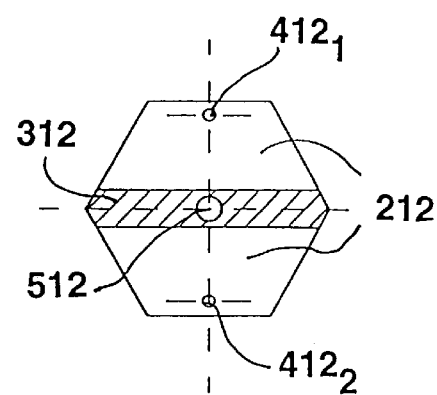
Figure 13:
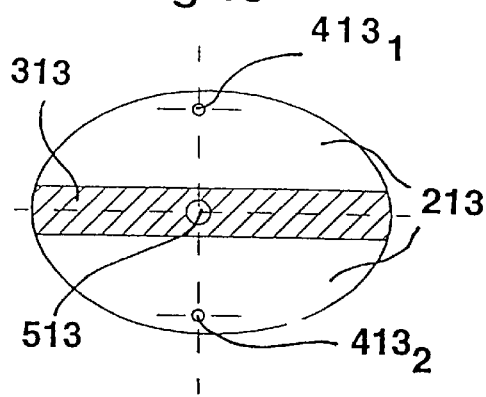
Figure 14:
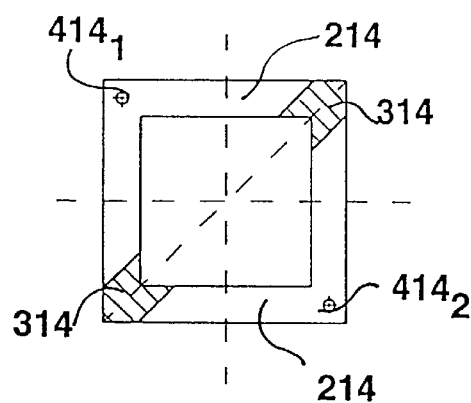
Figure 15:
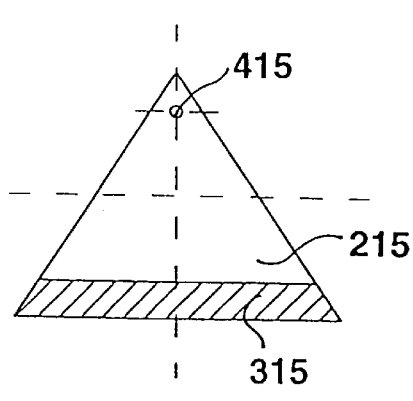
Figure 16:
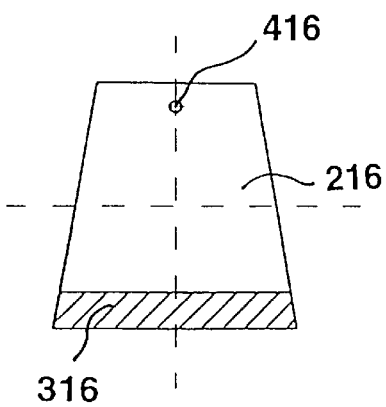
Figure 17:
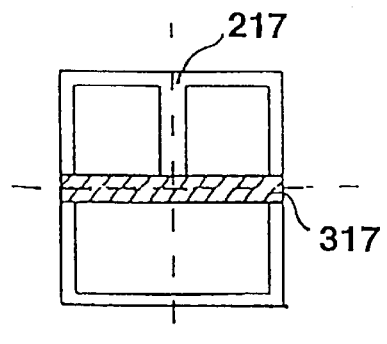
Figure 18:
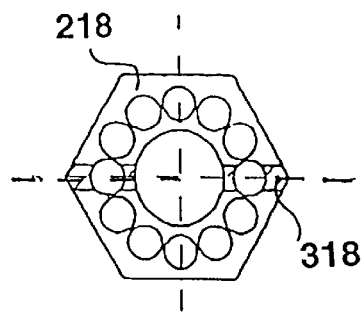
Figure 19:
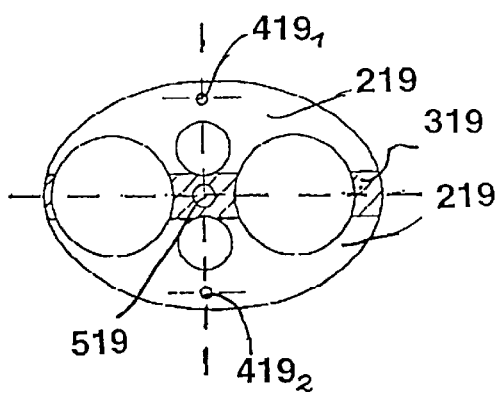
Figure 20:
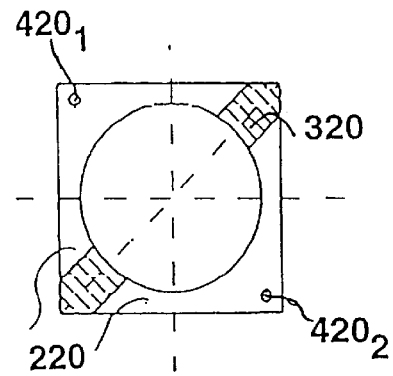
Figure 21:
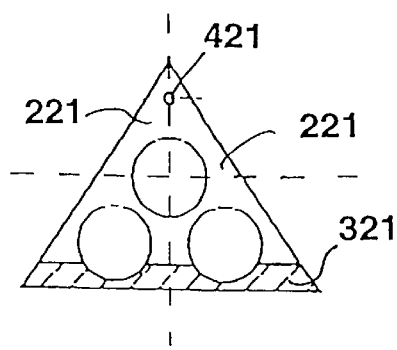
Figure 22:
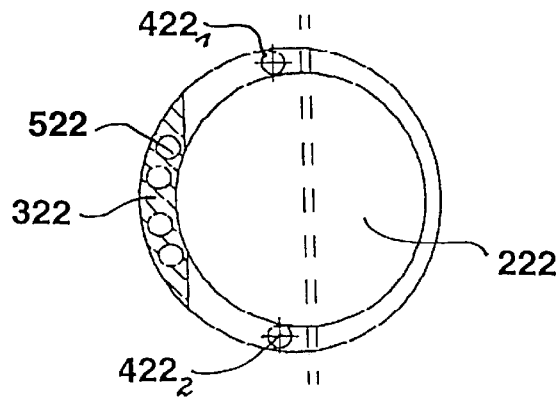
Figure 23:
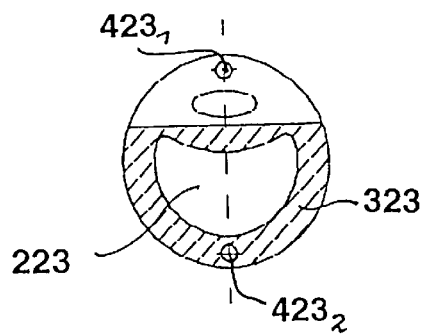

In FIGS. 11–23, different cross-sectional forms of blocks of material are shown at right angles to a longitudinal axis not identified by reference numeral in these drawings (but extending at right angles to the plane of the drawing); these blocks take the form of polygons, specifically a square in FIGS. 11, 14, 17 and 20 and a hexagon in FIGS. 12 and 18, an ellipse in FIGS. 13 and 19, an equilateral triangle in FIGS. 15 and 21, and an isosceles trapezoid in FIG. 16, and a circular form as in FIGS. 22 and 23.

In FIGS. 11–23, the various continuous, closed conduits are identified by the digit 5 plus the number of the particular drawing figure. The same applies to the bores diametrically opposite one another, which begin with the digit 4 and then the number corresponding to that of the applicable drawing figure. The remaining residual cross-sectional regions are identified first with reference numeral 3 and then with the number corresponding to the particular drawing figure. The same applies to the designation for the segments, which begins with the digit 2, followed by the number of the applicable drawing figure. For the rest, both the details and the special disposition and embodiment of the various parts can easily be seen from the various cross-sectional views in FIGS. 11–23, so that these drawings need not be described in further detail here.

I claim:

1. A flexible structure for medical technology use with pressure- or tension-exerting means for exerting pressure or tension, the structure comprising:

a circular- or polygonal-cylindrical block of material and characterized in that a number n of notches in the circular- or polygonal-cylindrical block of material, are formed parallel to and equidistant from one another, at right angles or an acute angle to a center longitudinal axis of the block, being made so deep that for joining (n+1) segments, a continuous, residual cross-sectional region remains between opposed ends of the two groups of notches, symmetrically to the longitudinal axis (10) of the block;

diametrically opposed, aligned bores are provided in the segments to accommodate two of the pressure- or tension-exerting means; and a continuous, closed conduit formed concentrically with the center axis of the block of material, the conduit comprising a surgical conduit.

2. The structure of claim 1, characterized in that the number n of notches (12a, 12b) in a circular-cylindrical block of material (1) are formed parallel to and equidistant from one another, at right angles or an acute angle to the longitudinal axis of the block, beginning at two diametrically opposed jacket lines ($10_1$, $10_2$), being made so deep that for joining (n+1) segments (22), a continuous, residual cross-sectional region (32) remains between the opposed ends of the two groups (12a, 12b) of notches, symmetrically to the longitudinal axis (10) of the block, to accommodate two pressure- or tension-exerting means, diametrically opposed, aligned bores ($42_1$, $42_2$) are provided in the segments and to form surgical conduit, a continuous, closed conduit (52) is formed concentrically with the center axis of the block of material.

3. The structure of claim 2, characterized in that the flexible structure preferably comprises viscoplastic plastic, such as polytetrafluoroethylene (PTFE), polyamide (PA), polyethylene (PE) or polyvinylchloride (PVC).

4. The structure of claim 3, characterized in that the flexible structure comprises metal special alloys, such as shape memory alloys or titanium alloys.

5. The structure of claim 2, characterized in that to form a surgical conduit, suction and/or flushing conduits, and conduits for receiving fiber optics and the like, continuous, closed conduits (52) and bores ($52_1$, $52_2$) aligned with one another are formed.

6. The structure of claim 5, characterized in that the flexible structure preferably comprises viscoplastic plastic, such as polytetrafluoroethylene (PTFE), polyamide (PA), polyethylene (PE) or polyvinylchloride (PVC).

7. The structure of claim 5, characterized in that the flexible structure comprises metal special alloys, such as shape memory alloys or titanium alloys.

8. The structure of claim 1, characterized in that the number n of notches (13a, 13b) in a preferably circularcylindrical block of material (1) are formed parallel to and equidistant from one another, at right angles or an acute angle to the longitudinal axis (10) of the block, alternatingly beginning at two each of diametrically opposed jacket lines ($10_1$, $10_2$, $10_3$, $10_4$) offset by 90° along a circular circumferential line, being made so deep that for joining the (n+1) segments (23), an approximately square residual cross-sectional region (33) extending longitudinally over the entire block of material, symmetrically to the longitudinal axis (10) of the block, remains between the opposed ends of the two groups of notches (13a, 13b) offset by 90° from one another to accommodate two pressure- or tension-exerting means, diametrically opposed, aligned bores ($43_1$, $43_2$) are provided in the segments and to form a surgical conduit, a continuous, closed conduit (53) is formed concentrically with the center axis of the block of material.

9. The structure of claim 8, characterized in that the flexible structure preferably comprises viscoplastic plastic, such as polytetrafluoroethylene (PTFE), polyamide (PA), polyethylene (PE) or polyvinylchloride (PVC).

10. The structure of claim 8, characterized in that the flexible structure comprises metal special alloys, such as shape memory alloys or titanium alloys.

11. The structure of claim 1, characterized in that to accommodate one or more actuators, the width of notches (19) which are rectangular or square in cross section is a multiple of the width of solid segments (29) formed at right angles to the longitudinal axis (1), to accommodate two pressure- or tension-exerting means, diametrically opposed, aligned bores ($49_1$, $49_2$) are provided in the segments and to form surgical conduit, a continuous, closed conduit (59) is formed concentrically with the center axis of the block of material.

12. The structure of claim 1, characterized in that the notches (110) seen in side view have the form of triangles, preferably equilateral triangles, and the complementary segments (210) are joined together to form a one-piece, bendable structure by an approximately rectangular residual cross-sectional region (310) extending longitudinally of the block (1) over the entire length thereof, to accommodate two pressure- or tension-exerting means, diametrically opposed, aligned bores ($41_{01}$, $41_{02}$) are provided in the segments and to form surgical conduit, a continuous, closed conduit (510) is formed concentrically with the center axis of the block of material.

13. The structure of claim 1, characterized in that the block of material, at right angles to its longitudinal axis, has the form of a square, each block of material is subdivided by n notches into (n+1) segments (211), which via residual cross-sectional region (311) form a one-piece, flexible, bendable structure, to accommodate two pressure- or tension-exerting means, diametrically opposed, aligned bores ($411_1$, $411_2$) are provided in the segments and to form surgical conduit, a continuous, closed conduit (511) is formed concentrically with the center axis of the block of material.

14. The structure of claim 1, characterized in that the block of material, at right angles to its longitudinal axis, has the form of a hexagon, each block of material is subdivided by n notches into (n+1) segments (212), which via residual cross-sectional region (312) form a one-piece, flexible, bendable structure, to accommodate two pressure- or tension-exerting means, diametrically opposed, aligned bores ($412_1$, $412_2$) are provided in the segments and to form surgical conduit, a continuous, closed conduit (512) is formed concentrically with the center axis of the block of material.

15. The structure of claim 1, characterized in that the block of material, at right angles to its longitudinal axis, has the form of an ellipse, each block of material is subdivided by n notches into (n+1) segments (213), which via residual cross-sectional region (313) form a one-piece, flexible, bendable structure, to accommodate two pressure- or tension-exerting means, diametrically opposed, aligned bores ($413_1$, $413_2$) are provided in the segments and to form surgical conduit, a continuous, closed conduit (513) is formed concentrically with the center axis of the block of material.

16. The structure of claim 1, characterized in that the flexible structure preferably comprises viscoplastic plastic, such as polytetrafluoroethylene (PTFE), polyamide (PA), polyethylene (PE) or polyvinylchloride (PVC).

17. The structure of claim 1, characterized in that the flexible structure comprises metal special alloys, such as shape memory alloys or titanium alloys.

18. A flexible structure for medical technology use with pressure- or tension-exerting means for exerting pressure or tension, the structure comprising:

a circular- or polygonal-cylindrical block of material and characterized in that a number n of notches in the circular- or polygonal-cylindrical block of material, are formed parallel to and equidistant from one another, at right angles or an acute angle to a center longitudinal axis of the block, being made so deep that for joining (n+1) segments, a continuous, residual cross-sectional region remains between opposed ends of the two groups of notches, symmetrically to the longitudinal axis (10) of the block;

diametrically opposed, aligned bores are provided in the segments to accommodate two of the pressure- or tension-exerting means; and a continuous, closed conduit formed concentrically with the center axis of the block of material, the conduit comprising a surgical conduit;

wherein, the block of material (1) is in the form of a turned part, the block (1) is subdivided by the number (n) of notches (16), which are disposed parallel to one another and at equal or unequal spacings from one another, into (n+1) segments (26), which are joined together by a central, approximately circular residual cross-sectional region (36), so that a onepiece bendable structure is thereby formed.

\* \* \* \* \*